United States Patent [19]
Doya et al.

[11] Patent Number: 4,918,196
[45] Date of Patent: Apr. 17, 1990

[54] PROCESS FOR RECIMIZATION OF AN OPTICALLY ACTIVE ALPHA-AMINO ACID AMIDES AND PROCESS FOR PRODUCING OPTICALLY ACTIVE ALPHA-AMINO ACIDS

[75] Inventors: Masaharu Doya; Toshio Kondo; Hideo Igarashi; Takako Uchiyama, all of Niigata, Japan

[73] Assignee: Mitsubishi Gas Chemical Company, Inc., Tokyo, Japan

[21] Appl. No.: 831,915

[22] Filed: Feb. 21, 1986

[30] Foreign Application Priority Data

Feb. 25, 1985 [JP] Japan .................................. 60-36001
Jun. 21, 1985 [JP] Japan ................................ 60-135462

[51] Int. Cl.$^4$ .................. C07D 233/90; C07D 209/20; C07C 103/183; C07C 103/28
[52] U.S. Cl. ................................ 548/342; 548/205; 548/494; 548/495; 548/498; 546/323; 564/162; 564/164; 564/165; 564/198
[58] Field of Search ............... 564/162, 164, 165, 198; 546/323; 548/205, 342, 494, 495, 498

[56] References Cited

U.S. PATENT DOCUMENTS 3,213,106 10/1965 Sasaji et al. ......................... 548/498

FOREIGN PATENT DOCUMENTS 58-17741  4/1983  Japan .................................. 564/198
59-159789 9/1984  Japan .................................. 435/106
60-36446  2/1985  Japan .................................. 435/106
60-184053 9/1985  Japan .................................. 546/323

OTHER PUBLICATIONS

Boesten et al., Chem. Abstracts, vol. 87, (17), Abst. No. 87:136,381d, Oct. 24, 1977.
Boesten, Chem. Abstracts, vol. 93, (5), Abst. No. 93:47200a, Aug. 4, 1980.
Kiuchi et al., Chem. Abstracts, vol. 105, (25), Abst. No. 105:224,600v, Dec. 22, 1986.

Primary Examiner—Alan L. Rotman
Attorney, Agent, or Firm—Wenderoth, Lind & Ponack

[57] ABSTRACT

A process for optically isomerizing an optically active alpha-amino acid amide comprising heating a D-alpha-amino acid amide or an L-alpha-amino acid amide in the presence of a strongly basic compound; and a process for producing an L-alpha-amino acid, which comprises (1) subjecting a D,L-alpha-amino acid amide or a mixture of a major amount of a D-alpha-amino acid amide and a minor amount of an L-alpha-amino acid amide to the action of a microorganism having the ability to hydrolyze the L-alpha-amino acid to obtain a hydrolyzate containing the L-alpha-amino acid and D-alpha-amino acid, (2) separating the L-alpha-amino acid from the hydrolyzate and recovering the remaining D-alpha-amino acid amide.

(3) heating all or part of the recovered D-alpha-amino acid amide in the presence of a strongly basic substance to obtain a D,L-alpha-amino acid amide or a mixture of a major amount of the D-alpha-amino acid amide and a minor amount of the L-alpha-amino acid amide, and (4) recycling the D,L-alpha-amino acid amide or the mixture to step (1) as part or all of the starting material.

11 Claims, No Drawings

PROCESS FOR RECIMIZATION OF AN OPTICALLY ACTIVE ALPHA-AMINO ACID AMIDES AND PROCESS FOR PRODUCING OPTICALLY ACTIVE ALPHA-AMINO ACIDS

This invention relates to a process for optically isomerizing an optically active alpha-amino acid amide and a process for producing an optically active alpha-amino acid. More specifically, this invention relates to a process for optically isomerizing an optically active alpha-amino acid amide, and a process for producing an L-alpha-amino acid including a step of optically isomerizing a D-alpha-amino acid amide to an L-alpha-amino acid amide.

Hydrolysis of an alpha-aminonitrile is known as a method for producing D,L-alpha-amino acid amides.

Japanese Patent Publication No. 17741/1983 discloses a process for producing an alpha-amino acid amide which comprises hydrolyzing an alpha-aminonitrile in the presence of not more than 0.01 mole, per mole of alpha-aminonitrile, of a basic substance at a reaction temperature of not more than 40° C. while maintaining the pH of the reaction mixture at more than 14 by adding a ketone to the reaction system so that the pH of the reaction mixture exceeds 14.

Physicochemical and biochemical methods have been known for the optical resolution of D,L-alpha-amino acids. The latter advantageously has high selectivity, and for example, the following two methods have been commercially accepted.

(1) A method which comprises acylating a D,L-alpha-amino acid, and subjecting the resulting N-acylation product of the D,L-alpha-amino acid to the action of an enzyme acylase possessed by a microorganism as schematically shown below.

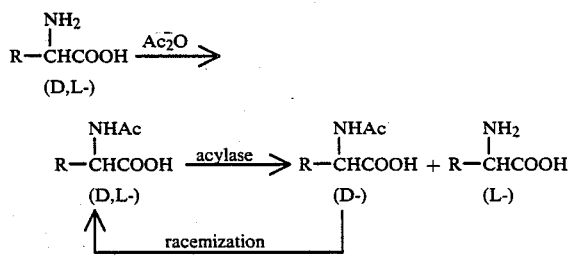

(2) A method which comprises subjecting a hydantoin derivative of a D,L-alpha-amino acid successively to the action of hydantoinase and hydrolase enzymes possessed by microorganisms.

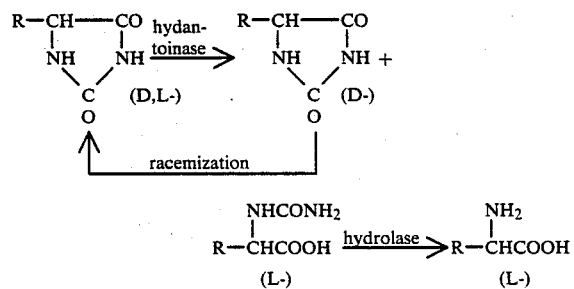

The method (1), however, requires the use of an expensive acylating agent, and has the defect that the step of racemizing the D-N-acyl-alpha-amino acid after separation of the L-alpha-amino acid is complex. The method (2) has the defect that since the hydantoin ring of the starting material is relatively stable, it is difficult to decompose with the hydrolase.

On the other hand, methods have been known to produce L-alpha-amino acids which comprise subjecting a D,L-alpha-amino acid amide represented by the following formula

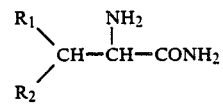

wherein $R_1$ and $R_2$ are identical or different and each represents a hydrogen atom, a lower alkyl group, a substituted lower alkyl group, a phenyl group, a substituted phenyl group, a hydroxyl group, a carboxyl group, a carboxamide group or a mercapto group, to the action of a culture broth, living cells or cell treated products of a microorganism of a particular genus having the ability to hydrolyze L-alpha-amino acid amides (Japanese Laid-Open Patent Publications Nos. 159789/1984 and 36446/1985).

There was also suggested a method of separating an L-alpha-amino acid selectively from a liquid obtained by the biochemical hydrolysis of a D,L-alpha-amino acid amide as above and containing the L-alpha-amino acid and a D-alpha-amino acid amide, which comprises subjecting the above liquid to ion-exchange electrodialysis in the presence of ammonia (see Japanese Laid-Open Patent Publication No. 184053/1985).

For racemization of the D-alpha-amino acid amide obtained after selective separation and recovery of the L-alpha-amino acid, a method is known which comprises heating an optically active phenyl- or substituted phenyl-glycine amide in a solvent in the presence of a ketone and an acid having a dissociation constant of not more than $1.3 \times 10^{-4}$ (see Japanese Laid-Open Patent Publication No. 71442/1977). This method, however, has the defect that it requires the use of the expensive ketone and acid, the reaction time is long and by-products are formed, and moreover the recovery of the alpha-amino acid amide from the reaction system is complex.

It is an object of this invention to provide an industrially advantageous novel process for optically isomerizing an optically active alpha-amino acid amide.

It is another object of this invention to provide a process for optically isomerizing an optically active alpha-amino acid amide by heating it in the presence of a strongly basic compound.

Still another object of this invention is to provide an industrially advantageous process for producing an L-alpha-amino acid, which comprises selectively hydrolyzing a D,L-alpha-amino acid amide by a biochemical technique to obtain an L-alpha-amino acid, recovering the remaining D-alpha-amino acid amide, heating the D-alpha-amino acid amide in the presence of a strongly basic compound to isomerize it optically, and recycling the optically isomerized mixture as the starting material in the hydrolyzation.

Further objects and advantages of this invention will become apparent from the following description.

According to this invention, these objects and advantages of the invention are achieved by a process for optically isomerizing an optically active alpha-amino acid amide, which comprises heating a D-alpha-amino acid amide represented by the following formula (1)-a

wherein R represents a substituted or unsubstituted lower alkyl group, a substituted or unsubstituted phenyl group, a furyl group, a pyridyl group, a thiazolyl group, an imidazolyl group or an indolyl group, or an L-alpha-amino acid amide represented by the following formula (1)-b

wherein R is as defined for (1)-a,
in the presence of a strongly basic compound.

The optically active alpha-amino acid amide used in the optical isomerization process or the racemization process (to be referred to as the optical isomerization process) of this invention is the D-alpha-amino acid amide of formula (1)-a or the L-alpha-amino acid amide of formula (1)-b. For practical purposes, the D-alpha-amino acid is preferred.

In formulae (1)-a and (1)-b, R represents a substituted or unsubstituted lower alkyl group, a substituted or unsubstituted phenyl group, a furyl group, a pyridyl group, a thiazolyl group, an imidazolyl group or an indolyl group.

The lower alkyl group may be linear or branched, and preferably has 1 to 4 carbon atoms. Examples of the unsubstituted lower alkyl group are methyl, ethyl, n-propyl, isopropyl, n-butyl, isobutyl, sec-butyl and tert-butyl.

The substituent on the substituted lower alkyl group may include those known in the chemistry of amino acids, such as hydroxy, methoxy, mercapto, methylmercapto, amino, guanyl, carboxamide, halogens (e.g., chloro), phenyl, hydroxyphenyl, imidazolyl or indolyl. Examples of the substituent on the substituted phenyl group may be those given above for the substituted lower alkyl group.

Examples of the amino acid amide of formulae (1)-a and (1)-b include alaninamide, valinamide, leucinamide, isoleucinamide, serinamide, threoninamide, cysteinamide, cystinamide, methioninamide, lysinamide, argininamide, aspartic amide, glutaminamide, phenylglycinamide, phenylalaninamide, tyrosinamide, tryptophanamide and histidinamides in D- and L-forms.

The optical isomerizing process of this invention is carried out by heating the optically active alpha-amino acid amide in the presence of a strongly basic compound.

The strongly basic compound may be organic or inorganic. Organic quaternary ammonium compounds are preferably used as the organic strongly basic compound. For example, tetramethyl ammonium hydroxide, tetraethyl ammonium hydroxide and tetra-n-propyl ammonium hydroxide are used especially preferably. Alkali metal compounds and alkaline earth metal compounds are preferably used as the inorganic strongly basic compound. Examples of particularly preferred inorganic basic compounds include hydroxides such as sodium hydroxide, potassium hydroxide, lithium hydroxide, cesium hydroxide, rubidium hydroxide and barium hydroxide, and other various basic compounds such as sodium methylate, sodium ethylate, sodium amide, sodium hydride, sodium cyanide and potassium cyanide.

It is also possible to add a metal element such as lithium, sodium, potassium or barium to the reaction system, and form a strongly basic metal compound in situ.

The strongly basic compound is used in an amount of preferably 0.001 to 0.5 mole, especially preferably 0.01 to 0.1 mole, per mole of the optically active alpha-amino acid amide.

The optical isomerization in accordance with this invention can be carried out in the presence or absence of a solvent. The use of solvent generally enables the isomerization reaction temperature to be lowered, and thus brings about the advantage that side-reactions which may occur owing to high isomerization reaction temperatures can be inhibited or prevented. The reaction solvent is nonreactive with the alpha-amino acid amide, alpha-amino acid and strongly basic compound. Examples include hydrocarbons such as gasoline, kerosene, hexane, heptane, cyclohexane, ligroin, benzene, toluene, xylene, mesitylene, cumene and cymene; alcohols such as n-butanol, isobutanol, n-amyl alcohol and isoamyl alcohol; and isobutyronitrile.

The solvent is used in an amount of preferably not more than 100 parts by weight, especially preferably 1 to 20 parts by weight, per part by weight of the optically active alpha-amino acid amide.

The optical isomerization reaction can be carried out at a temperature of, for example, 20° to 200° C., advantageously 50° to 150° C. The optical isomerization reaction (including racemization) is carried out usually under atmospheric pressure. It is also possible to operate under elevated or reduced pressure.

Desirably, the water content of the reaction mixture is as small as possible. The advantageous water content is not more than 1% by weight, especially not more than 0.1% by weight.

The reaction time varies depending mainly upon the type of the alpha-amino acid amide, the type and amount of the strongly basic compound, the type and amount of the solvent, and the reaction temperature. Sometimes, a period of 1 minute suffices, and at other times a period of as long as 3 hours may be required.

The D,L-alpha-amino acid amide or a mixture of the D-alpha-amino acid amide and L-alpha-amino acid amide one of which is present in a larger proportion than the other, which is present in the reaction mixture as obtained after the optical isomerization reaction may be separated and recovered by ordinary solid-liquid separating procedures, for example by removing the solvent under reduced pressure and collecting the precipitated crystals.

The optically isomerized alpha-amino acid amide so obtained sometimes contains a trace of the strongly basic compound, but may be used directly as a material to be optically resolved. When it is desired to remove the trace of the strongly basic compound, an acid is added to the reaction mixture as obtained by the optical isomerization reaction to precipitate the strongly acidic compound as a salt, and then remove the salt.

According to the present invention, there is also provided a process for producing an L-alpha-amino acid industrially advantageously by a series of steps in which the above process of this invention using the strongly basic compound for optical isomerization is applied to the optical isomerization of a D-alpha-amino acid amide.

Specifically, the process for producing an L-alpha-amino acid in accordance with this invention comprises (1) subjecting a D,L-alpha-amino acid amide or a mixture of a major amount of a D-alpha-amino acid amide and a minor amount of an L-alpha-amino acid amide to the action of a microorganism having the ability to hydrolyze the L-alpha-amino acid amide, a culture broth thereof or a treated product thereof to obtain a hydrolyzate containing the L-alpha-amino acid and D-alpha-amino acid amide, (2) separating the L-alpha-amino acid from the hydrolyzate and recovering the remaining D-alpha-amino acid amide, (3) heating all or part of the recovered D-alpha-amino acid amide in the presence of a strongly basic substance to obtain a D,L-alpha-amino acid amide or a mixture of a major amount of the D-alpha-amino acid amide and a minor amount of the L-alpha-amino acid amide, and (4) recycling the D,L-alpha-amino acid amide or the mixture to step (1) as part or all of the starting material.

These process steps will be described below in detail.

The first step is for hydrolyzing the L-alpha-aminoacid amide by subjecting an alpha-amino acid amide which is a mixture of a D-isomer and an L-isomer to the action of a microorganism having the ability to hydrolyze the L-isomer. The starting material used in the first step is a D,L-alpha-amino acid amide (racemic mixture) or a mixture of a D-alpha-amino acid amide and an L-alpha-amino acid amide in which the D-alpha-amino acid amide is larger in amount than the L-alpha-amino acid amide. There is no particular restriction on the manufacturing method and the quality of the starting mixture. For example, the D,L-alpha-amino acid amide may be produced by a method which comprises esterifying a synthesized D,L-alpha-amino acid, and amidating the resulting D,L-alpha-amino acid ester with liquid ammonia, or a method comprising hydrolyzing an L-alpha-aminonitrile. The former is unsatisfactory in that a D,L-alpha-amino acid containing an L-alpha-amino acid, the final product of the present invention, is used as a starting material. The latter method has a noteworthy advantage in that it uses the D,L-alpha-aminonitrile which can be easily produced from an aldehyde, hydrocyanic acid and ammonia which are widely used as industrial materials. Hence, the latter method is preferred. A particularly recommended process falling within the category of the latter method comprises hydrolyzing a D,L-alpha-aminonitrile in an aqueous medium in the presence of a basic substance and a ketone, as described in Japanese Patent Publication No. 17741/1983. This process is characterized in that the amount of the basic substance, for example inorganic bases such as sodium hydroxide and potassium hydroxide and organic bases such as organic quaternary ammonium compounds, e.g., tetramethyl ammonium hydroxide is adjusted to not more than 0.01 mole per mole of D,L-alpha-aminonitrile; a ketone such as acetone, methyl ethyl ketone, diethyl ketone, methyl isopropyl ketone or cyclohexanone is added to the reaction system so that the pH of the reaction mixture exceeds 14; and the hydrolysis reaction for producing a D,L-alpha-amino acid amide is carried out while maintaining the reaction temperature at not more than 40° C. and the pH of the reaction mixture at more than 14.

Usually, a pH meter including a glass electrode is used for the measurement of the p of the reaction mixture in the production of the D,L-alpha-amino acid amide. The pH of the reaction mixture "exceeding 14" can be indirectly determined by diluting the reaction mixture with a mixture of water and ketone having the same composition ratio as the water/ketone ratio in the reaction mixture, measuring the pH of the dilution by a pH meter, and adding $\log_{10}$ "dilution ratio" to the measured pH value. For example, when the reaction solution is diluted to 10 times and 100 times, respectively, the pH can be obtained by adding 1 and 2 respectively to the measured values directly read by the pH meter.

The D,L-alpha-aminonitrile hydrolysis reaction mixture is concentrated to remove acetone, and the resulting crude D,L-alpha-amino acid amide-containing residue may be used as the starting D,L-alpha-amino acid amide in step (1) either directly or after optionally purifying it by such a means as distillation or recrystallization.

The mixture containing a major amount of the D-alpha-amino acid amide and a minor amount of the L-alpha-amino acid amide which is used likewise as the starting material of step (1) will become apparent from the following description of step (3).

Preferred starting alpha-amino acid amides are, for example, compounds represented by the following formula (1)

wherein R represents a substituted or unsubstituted lower alkyl group, a substituted or unsubstituted phenyl group, a furyl group, a pyridyl group, a thiazolyl group, an imidazolyl group or an indolyl group. It should be understood that the alpha-amino acid amide of formula (1) is a racemic mixture of the D-alpha-amino acid amide of formula (1)-a and the L-alpha-amino acid amide of formula (1)-b or a mixture of these compounds in which the D-isomer exists in a larger amount than the L-isomer. The details of the alpha-amino acid amide of formula (1) will become apparent from the description of the optically active compounds of formulae (1)-a and (1)-b.

Microorganisms used in the biochemical hydrolysis of the D,L-alpha-amino acid amide or the mixture of a major amount of the D-alpha-amino acid amide and a minor amount of the L-alpha-amino acid amide are, for example, those belonging to the following genera. Typical species of these genera are given below, and it should be understood that the invention is not limited to the use of these typical examples of microorganisms.

(1) Genus Schizosaccharomyces: *Schizosaccharomyces japonicus* (ATCC 10660), and *Shizosaccharomyces pombe* (ATCC 16979).

(2) Genus Rhodosporidium: *Rhodosporidium toruloides* (IFO 0871), and *Rhodosporidium diobovatum* (IFO 1828).

(3) Genus Candida: *Candida humicola* (ATCC 14438), and *Candida albicans* (ATCC 10259).

(4) Genus Cryptococcus: *Cryptococcus laurentii* (ATCC 18803) and *Cryptococcus neoformans* (ATCC 32045).

(5) Genus Pityrosporum: *Pityrosporum pachydermatis* (IFO 0995), and *Pityrosporum ovale* (IFO 0656)

(6) Genus Rhodotorula: *Rhodotorula glutinis* (IFO 0389), and *Rhodotorula rubla* (IFO 0914).

(7) Genus Torulopsis: *Torulopsis candida* (IFO 0380).
(8) Genus Trichosporon: *Trichosporon cutaneum* (ATCC 28592), and *Trichosporon fermentans* (ATCC 10675).
(9) Genus Tremella: *Tremella fuciformis* (IFO 9316), and *Tremella aurantia* (IFO 9288).
(10) Genus Rhodospirillum: *Rhodospirillum rubrum* (ATCC 17031).
(11) Genus Rhodopseudomonas: *Rhodopseudomonas palustris* (ATCC 17001).
(12) Genus Aquaspirillum: *Aquaspirillum aquaticum* (ATCC 11330).
(13) Genus Mycrocyclus: *Mycrocyclus eburneus* (ATCC 21373).
(14) Genus Pseudomonas: *Pseudomonas rosea* (NCIB 10605).
(15) Genus Gluconobacter: *Gluconobacter cerinus* (IFO 3262).
(16) Genus Agrobacterium: *Agrobacterium radiobacter* (IFO 12664).
(17) Genus Alcaligenes: *Alcaligenes odorans* (ATCC 15554).
(18) Genus Achromobacter: *Achromobacter methanolophila* (ATCC 21452).
(19) Genus Acetobacter: *Acetobacter rancens* (IFO 3191).
(20) Genus Escherichia: *Escherichia coli* (IFO 3543).
(21) Genus Enterobacter: *Enterobacter cloacae* (IAM 12349).
(22) Genus Serratia: *Serrat marcescens* (IAM 1106).
(23) Genus Aeromonas: *Aeromonas hydrophila* (IAM 12333).
(24) Genus Flavobacterium: *Flavobacterium devorans* (ATCC 10829).
(25) Genus Paracoccus: *Paracoccus denitrificans* (IFO 12442)
(26) Genus Thiobacillus: *Thiobacillus sp.* (ATCC 25364).
(27) Genus Streptococcus: *Streptococcus faecalis* (IAM 1119).
(28) Genus Corynebacterium: *Corynebacterium fascians* (IFO 12077).
(29) Genus Arthrobacter: *Arthrobacter parraficum* (NRRL B-3453).
(30) Genus Microbacterium: *Microbacterium flavum* (NCIB 10071).
(31) Genus Nocardia: *Nocardia pseudosporangifera* (IAM 0501).
(32) Genus Mucor: *Mucor javanicus* (IFO 4569).
(33) Genus Rhizopus: *Rhizopus oryzae* (IFO 4706).
(34) Genus Aspergillus: *Aspergillus oryzae* (IFO 4075).
(35) Genus Penicillium: *Penicillium vinaceum* (IFO 5794).
(36) Genus Fusarium: *Fusarium solani* (IFO 5232).
(37) Genus Nadsonia: *Nadsonia fulvescens* (IFO 0666).
(38) Genus Hanseniaspora: *Hanseniaspora valbyensis* (IFO 0683).
(39) Genus Wickerhamia: *Wickerhamia fluorescens* (IFO 1116).
(40) Genus Saccharomyces: *Saccharomyces diastaticus* (IFO 1046).
(41) Genus Lodderomyces: *Lodderomyces elogisporus* (IFO 1676).
(42) Genus Pichia: *Pichia farinosa* (IFO 0574).
(43) Genus Hansenula: *Hansenula polymorpha* (IFO 0799).
(44) Genus Pachysolen: *Pachysolen tannophilus* (IFO 1007).
(45) Genus Citeromyces: *Citeromyces matritensis* (IFO 0651).
(46) Genus Debaryomyces: *Debaryomyces kloecheri* (IFO 0036).
(47) Genus Dekkera: *Dekkera intermedia* (IFO 1591).
(48) Genus Saccharomycopsis: *Saccharomycopsis lypolytica* (IFO 1549).
(49) Genus Lipomyces: *Lipomyces starkeyi* (IFO 1289).
(50) Genus Leucosporidium: *Leucosporidium frigidum* (IFO 1851).
(51) Genus Sporobolomyces: *Sporobolomyces roseum* (IFO 1037).
(52) Genus Sporidiobolus: *Sporidiobolus johnsonii* (IFO 6903).
(53) Genus Oosporidium: *Oosporidium margaritiferum* (IFO 1208).
(54) Genus Sterigmatomyces: *Sterigmatomyces indicus* (IFO 1844).
(55) Genus Trigonopsis: *Trigonopsis valiabilis* (IFO 0755).

The microorganisms listed above as typical examples are known, and can be easily obtained from depositories such as Institution for Fermentation OSAKA JAPAN (IFO, Japan), Institute of Applied Microbiology, University of Tokyo, Japan (IAM, Japan), The American Type Culture Collection (ATCC, U.S.A.), The National Collection of Industrial Bacteria (NCIB, Britain), and the Northern Regional Research and Laboratory (NRRL, U.S.A.).

Among the above microorganisms, those of the genera Pseudomonas, Cryptococus, Lodderomyces, Rhodosporidium and Pachysolen are preferred.

These microorganisms may be cultivated on media containing carbon sources and nitrogen sources which the microorganisms can assimilate and inorganic salts and nutrients which are essential to the individual microorganisms. To obtain high enzyme activity, it is effective to add a D,L-alpha-amino acid amide to the media in advance of cultivation. Preferably, this D,L-alpha-amino acid amide is one corresponding to the desired L-alpha-amino acid to be finally obtained.

The pH of the culture during cultivation is in the range of 4 to 10, and the cultivation temperature is 20° to 50° C. The cultivation is carried out aerobically for 1 day to 1 week.

The cultivated microorganisms are used in the reaction as the "culture broth", "cells such as separated cells or dried cells", or "a cell-treated product such as the cell debris or a purified enzyme". The cells or enzyme may be immobilized in a customary manner and then used in the reaction.

Preferably, the biochemical hydrolysis reaction of step (1) using the microbial cells, the culture broth or the cell treated product is carried out while adjusting the concentration of the D,L-alpha-amino acid amide or the mixture of a major amount of the D-alpha-amino acid amide and a minor amount of the L-alpha-amino acid amide in the reaction mixture to 1 to 40% by weight, particularly 2 to 20% by weight, using the microorganism in an amount of 0.005 to 10 parts by weight, especially 0.01 to 1 part by weight, on a dry substrate basis, per part by weight of the starting material, and maintaining the pH at 5 to 13, particularly 7 to 11, and the reaction temperature at 20° to 70° C., particularly 30° to 50° C.

By step (1), the L-alpha-amino acid amide in the starting material is hydrolyzed to an L-alpha-amino acid. Hence, the reaction product of step (1) at least contains the L-alpha-amino acid and the D-alpha-amino acid amide.

Thereafter, in step (2), the L-alpha-amino acid is separated from the hydrolysis reaction product, and the D-alpha-amino acid amide is recovered. For example, the microbial cells are optionally removed from the hydrolysis reaction product by a conventional solid-liquid separating means such as centrifugal separation or filtration, and the residues subjected to ion-exchange electrodialysis to separate the L-alpha-amino acid. Furthermore, the L-alpha-amino acid is crystallized from the dialyzate, or the dialyzate is concentrated under reduced pressure. Then, ethanol is added to the concentrated dialyzate to precipitate the L-alpha-amino acid. The precipitated L-alpha-amino acid is collected by filtration, or can be easily separated, for example, by crystallization from the residue left after solvent extraction of the D-alpha-amino acid amide to be described.

The D-alpha-amino acid amide can be easily recovered by concentrating the residue left after separation of the L-alpha-amino acid from the biochemical hydrolysis reaction mixture, or by solvent extraction from the hydrolysis reaction mixture from which the microbial cells have been separated.

According to the process of this invention, the whole or part of the D-alpha-amino acid amide recovered in step (2) is then optically isomerized in step (3). This optical isomerization is carried out in the presence of a strongly basic compound under the same conditions as in the optical isomerization reaction of this invention described hereinabove. Step (3) thus can give a D,L-alpha-amino acid amide (racemic mixture) or a mixture o a major amount of the D-alpha-amino acid amide and a minor amount of the L-alpha-amino acid amide by the optical isomerization reaction of the D-alpha-amino acid amide.

In step (4) of the process of this invention, the optical isomerization reaction product obtained in step (3) is recycled to step (1), and used as part or the whole of the starting material in step (1).

The following examples illustrate the present invention more specifically. It should be understood however that the invention is in no way limited to these examples alone.

EXAMPLE 1

A 25 ml three-necked flask equipped with a stirrer, a thermometer and a reflux condenser was charged with 2 g of D-phenylalaninamide, 8 g of toluene and 0.02 g of sodium hydroxide, and the mixture was stirred at 110° C. for 0.5 hour.

After the reaction, the reaction mixture was analyzed by liquid chromatography. The ratio of the remaining phenylalaninamide was 97%, and the ratio of racemization of the D-phenyalaninamide was 95%.

The ratio of the remaining phenylalaninamide and the ratio of racemization of the D-phenylalaninamide were calculated in accordance with the following equation.

Ratio of the remaining phenylalaninamide (%) =

$$\frac{\text{Amide after racemization}}{\text{Amide charged}} \times 100$$

Ratio of racemization of D-phenylalaninamide (%) =

$$\frac{\text{L-amide in the racemization reaction mixture}}{\text{L-amide + D-amide in the racemization reaction mixture}} \times 100$$

A racemization ratio of 100% means that the amount of the L-alpha-amino acid amide in the racemization reaction mixture is equal to that of the D-alpha-amino acid amide.

The above percentages are either by mole or by weight.

In the following examples, the ratio of the remaining alpha-amino acid amide and the ratio of racemization of the alpha-amino acid amide were calculated in the same way as above.

EXAMPLES 2-11

In each run, Example 1 was repeated except that each of the strongly basic substance indicated in Table 1 was used. The results are also shown in Table 1.

TABLE 1

| | Strongly basic substance | | Results | |
|---|---|---|---|---|
| Example | Compound | Amount (g) | Ratio of remaining amide (%) | Ratio of racemization (%) |
| 2 | Potassium hydroxide | 0.02 | 94 | 92 |
| 3 | Barium hydroxide | 0.06 | 96 | 80 |
| 4 | Sodium methylate | 0.02 | 93 | 85 |
| 5 | Sodium amide | 0.02 | 92 | 83 |
| 6 | Tetraethyl ammonium hydroxide | 0.05 | 91 | 78 |
| 7 | Lithium hydroxide | 0.05 | 84 | 89 |
| 8 | Cesium hydroxide | 0.12 | 92 | 86 |
| 9 | Potassium cyanide | 0.05 | 89 | 75 |
| 10 | Sodium hydride | 0.005 | 96 | 77 |
| 11 | Lithium | 0.04 | 79 | 80 |

EXAMPLES 12-21

In each run, Example 1 was repeated except that the solvents indicated in Table 2 was used in the amounts indicated, and the reaction temperature and time were varied as indicated in Table 2. The results are shown in Table 2.

TABLE 2

| | Solvent | | Reaction conditions | | Results | |
|---|---|---|---|---|---|---|
| Example | Compound | Amount (g) | Temperature (°C.) | Time (hours) | Ratio of remaining amide (%) | Ratio of racemization (%) |
| 12 | Heptane | 8 | 98 | 0.5 | 97 | 92 |
| 13 | Cyclohexane | 8 | 80 | 0.5 | 97 | 92 |
| 14 | Benzene | 8 | 80 | 0.5 | 96 | 88 |

TABLE 2-continued

| | Solvent | | Reaction conditions | | Results | |
|---|---|---|---|---|---|---|
| | | | Temperature | Time | Ratio of remaining amide | Ratio of racemization |
| Example | Compound | Amount (g) | (°C.) | (hours) | (%) | (%) |
| 15 | m-Xylene | 8 | 139 | 0.5 | 97 | 96 |
| 16 | p-Cymene | 2 | 177 | 2 (minutes) | 95 | 87 |
| 17 | n-Butanol | 8 | 117 | 0.5 | 92 | 93 |
| 18 | i-Butanol | 8 | 107 | 0.5 | 93 | 92 |
| 19 | n-Amyl alcohol | 4 | 138 | 2 | 90 | 94 |
| 20 | i-Amyl alcohol | 4 | 132 | 2 | 92 | 93 |
| 21 | iso-Butyronitrile | 8 | 108 | 3 | 90 | 86 |
| 22 | None | — | 110 | 0.5 | 86 | 57 |

EXAMPLES 23–30

In each run, Example 1 was repeated except that 1 g of each of the D-alpha-amino acid amides indicated in Table 3 was used, the amounts of sodium hydroxide and toluene were changed to 0.1 g and 9 g, respectively, and the reaction time was changed to 1 hour. The results are shown in Table 3.

TABLE 3

| | | Results | |
|---|---|---|---|
| Example | Type of D-alpha-amino acid amide | Ratio of remaining amide (%) | Ratio of racemization (%) |
| 23 | D-phenylalaninamide | 94 | 99 |
| 24 | D-valinamide | 95 | 97 |
| 25 | D-leucinamide | 95 | 95 |
| 26 | D-methioninamide | 93 | 98 |
| 27 | D-phenylglycinamide | 94 | 99 |
| 28 | D-tryptophanamide | 93 | 99 |
| 29 | D-alaninamide | 96 | 100 |
| 30 | D-isoleucinamide | 95 | 98 |

EXAMPLE 31

A 500 ml three-necked flask equipped with a stirrer, a thermometer and a reflux condenser was charged with 50 g of D-phenylalaninamide, 200 g of toluene and 0.36 g of sodium hydroxide, and the mixture was stirred at 110° C. for 1 hour. The reaction mixture was cooled to 20° C., and the precipitated crystals were filtered, washed with 20 ml of cold methanol and dried to give 48.0 g (recovery ratio 96.0%) of white crystals.

The elemental analysis values of the crystals were C 65.86% by weight, H 7.30% by weight, and N 16.98% by weight. The crystals had a specific rotation, $[\alpha]_D^{20}$, of ±0 (c=2, $H_2O$).

The calculated elemental analysis values of the starting D-phenylalaninamide were C 65.83% by weight, H 7.37% by weight, and N 17.05% by weight. It had a specific rotation, $[\alpha]_D^{20}$, of −18.0 (c=2, $H_2O$).

EXAMPLE 32

Example 24 was repeated except that L-valinamide was used as the starting material.

Analysis of the reaction product mixture by liquid chromatography showed that the ratio of remaining valinamide was 96%, and the ratio of racemization of L-valinamide was 97%.

The foregoing examples demonstrate that according to the process of this invention, optically active alpha-amino acid amides can be racemized industrially advantageously, and therefore the optically active amino acid amides can be used efficiently as a material for optically active alpha-amino acids.

EXAMPLE 33

(A) A 5-liter three-necked flask equipped with a stirrer and a thermometer was charged with 981.5 g of 1-isopropylaminoacetonitrile, 901 g of water, 581 g of acetone and 20 g of a 20% by weight aqueous solution of sodium hydroxide, and the mixture was stirred for 8 hours at 20° C. The pH of the reaction solution was 15.3 at the start of the reaction, gradually decreased, and reached 14.4 at the end of the reaction.

After the reaction, acetone was removed from the reaction mixture by distillation under reduced pressure to give 1812.5 g of an aqueous solution containing D,L-valinamide. The content of D,L-valinamide in the resulting aqueous solution, as analyzed by liquid chromatography, was 63.8% by weight. The yield of D,L-valinamide based on the 1-isopropylaminoacetonitrile charged was 99.5 mole %.

(B-1) A seed culture medium containing 1.0% by weight of glucose, 1.0% by weight of peptone and 1.0% by weight of yeast extract was prepared. One hundred milliliters of the seed culture medium was put in an Erlenmayer flask, and sterilized. Then, as a seed microorganism, *Pseudomonas rosea* (NCIB 10605) was inoculated in the culture medium, and cultivated with shaking at 30° C. for 48 hours to obtain a seed culture.

The seed culture was transferred to 2 liters of a main culture medium having the following composition, and cultivated at 30° C. for 48 hours with aeration and agitation.

| Composition of the main culture medium | |
|---|---|
| Glucose | 1.0% by weight |
| Peptone | 0.5 by weight |
| Yeast extract | 0.5 by weight |
| $KH_2PO_4$ | 0.1 by weight |
| $MgSO_4.7H_2O$ | 0.04 by weight |
| $FeSO_4.7H_2O$ | 0.001 by weight |
| $MnCl_2.4H_2O$ | 0.001 by weight |
| D,L-valinamide | 0.5 by weight |
| pH | 7 by weight |

Then, the culture broth was centrifuged to obtain 90 g of living cells which had a water content of 82% by weight.

(B-2) The D,L-valineamide-containing aqueous solution obtained in (A) above (181.3 g) and 390 g of water were weighed and put into a 1-liter Erlenmeyer flask, and 6.4 g of the living cells obtained in (B-1) above were added. The mixture was stirred at 40° C. for 22 hours.

After the reaction, the cells were removed from the reaction mixture by centrifugal separation, and water was removed under reduced pressure. Then, 200 ml of toluene was added to dissolve D-valinamide under heat. The insoluble material was collected by filtration, and washed with a small amount of hot toluene to give white crystals of L-valine. The weight of the resulting crystals after drying was 58.3 g, and the crystals had a specific rotation, $[\alpha]_D^{20}$, of +28.5 (6N—HCl, c=8). The yield of L-valine was 49.7 mole % based on the starting 1-isopropylaminoacetonitrile.

After separation of the crystals, the filtrate weighed 220 g. Analysis by liquid chromatography showed that it contained 57.6 g of D-valinamide.

(C) A 500 ml three-necked flask equipped with a stirrer, a thermometer and a reflux condenser was charged with all the D-valinamide-containing toluene solution (filtrate) recovered in (B-2) and 0.50 g of sodium hydroxide, and the mixture was stirred at 110° C. for 0.5 hour.

After the reaction, the reaction mixture was cooled to precipitate crystals of D,L-valinamide, and the resulting crystals were collected by filtration. The weight of the crystals after drying was 57.3 g. The crystals were analyzed by liquid chromatography, and it was found that the ratio of remaining D,L-valinamide was 97%, and the ratio of racemization of D-valinamide was 96%.

(D) A 1-liter Erlenmayer flask was charged with all the D,L-valinamide obtained in (C) above and 423.3 g of water. Furthermore, 90.7 g of the D,L-valinamide-containing aqueous solution obtained in (A) above and 6.4 g of the living cells obtained in (B-1) were added, and the same reaction and work-up as in (B-2) above were carried out.

The weight of the resulting L-valine crystals after drying was 55.6 g, and they had a specific rotation, $[\alpha]_D^{20}$, of +28.2 (6N—HCl, c=8). The yield of L-valine based on 1-isopropylaminoacetonitrile, the starting material corresponding to the newly added D,L-valinamide, was 94.9 mole %.

The filtrate after separation of the crystals weighed 222 g, and analysis by liquid chromatography showed that it contained 57.7 g of D-valinamide.

The operations of (C) and (D) were repeated three times using the D-valinamide-containing toluene solution recovered as above. The yield of L-valine, based on the starting 1-isopropylaminoacetonitile corresponding to the newly added D,L-valinamide was 95.2 to 94.8 mole %, and L-valine had a specific rotation, $[\alpha]_D^{20}$, of +28.2 to +28.1.

EXAMPLE 34

(A) A 3-liter three-necked flask equipped with a stirrer and a thermometer was charged with 701 g of 1-methylaminoacetonitrile, 541 g of water, 721 g of methyl ethyl ketone and 10 g of a 20% by weight aqueous solution of sodium hydroxide, and the mixture was stirred at 20° C. for 2 hours. The pH of the reaction solution was 15.2 at the start of the reaction, and 14.9 at the end of the reaction.

After the reaction, methyl ethyl ketone was removed from the reaction mixture by distillation under reduced pressure to give 998 g of a D,L-alaninamide-containing aqueous solution. The content of D,L-alaninamide content of the D,L-alaninamide-containing aqueous solution, as analyzed by liquid chromatography, was 88.3% by weight, and the yield of D,L-alaninamide based on the 1-methylaminoacetonitrile charged was 100 mole %.

(B-1) The same cultivation as in Example 32 was carried out except that *Cryptococcus laurentii* (ATCC 18803) was used as the microorganism. The culture broth was centrifuged to give 76 g of living cells which had a water content of 76% by weight.

(B-2) 99.8 g of the D,L-alaninamide-containing aqueous solution obtained in (A) above and 322 g of water were weighed and put in a 500 ml Erlenmeyer flask. Furthermore, 18.3 g of the living cells obtained in (B-1) above were added, and the mixture was stirred at 40° C. for 10 hours.

After the reaction, the reaction mixture was centrifuged to remove the cells, and water was removed under reduced pressure 200 ml of benzene was added and D-alaninamide was dissolved under heat. The insoluble material was collected by filtration, and washed with a small amount of hot benzene to give white crystals of L-alanine. The weight of the crystals after drying was 44.5 g, and the crystals had a specific rotation, $[\alpha]_D^{20}$, of +14.7 (6 N—HCl, c=10). The yield of L-alanine based on the starting 1-methylaminoacetonitrile was 49.9 mole %.

The filtrate after separation of the crystals weighed 215 g, and analysis by liquid chromatography showed that it contained 43.7 g of D-alaninamide.

(C) A 500 ml three-necked flask equipped with a stirrer, a thermometer and a reflux condenser was charged with all the D-alaninemaide-containing benzene solution (filtrate) recovered in (B-2) and 3.7 g of cesium hydroxide, and the mixture was stirred at 80° C. for 2.0 hours.

After the reaction, the cesium hydroxide was removed from the reaction mixture by hot filtration, and benzene was removed by distillation under reduced pressure. D,L-alaninamide crystals were precipitated by cooling, and the precipitated crystals were collected by filtration. The weight of the crystals after drying was 42.9 g. Analysis of the crystals by liquid chromatography showed that the ratio of remaining alaninamide was 94%, and the ratio of racemization of D-alaninamide was 92%.

(D) A 500 ml Erlenmeyer flask was charged with all the alaninamide obtained in (C) above and 329 g of water, and 49.9 g of the D,L-alanimaide-containing aqueous solution obtained in (A) above and 18.3 g of the living cells obtained in (B-1) above were added, and the same reaction and work-up as in (B-2) above were carried out.

The weight of the resulting L-alanine crystals after drying was 40.8 g, and the crystals had a specific rotation, $[\alpha]_D^{20}$, of +14.7 (6N—HCl, c=10). The yield of L-alanine on the starting 1-methylaminoacetonitrile corresponding to the freshly added D,L-alaninamide was 91.6 mole %.

The filtrate after separation of the crystals weighed 218 g, and analysis by liquid chromatography showed that it contained 44.2 g of D-alaninamide.

The operations of (C) and (D) were repeated twice using the D-alaninamide-containing benzene solution recovered as above. The yield of L-alanine crystals based on the starting 1-methylaminoacetonitrile corresponding to the freshly added D,L-alaninamide was 92.1 to 91.7 mole %, and the L-alanine crystals had a specific rotation, $[\alpha]_D^{20}$, of +14.5 to +14.3.

EXAMPLE 35

(A-1) A 500 ml three-necked flask equipped with a stirrer and a thermometer was charged with 146.2 g of 1-benzylaminoacetonitrile, 146.2 g of water, 146.2 g of acetone and 2.0 g of a 20% by weight aqueous solution of sodium hydroxide, and the mixture was stirred at 20° C. for 1 hour. The pH of the reaction solution was 15.2 at the start of the reaction, and 15.0 at the end of the reaction.

After the reaction, the reaction mixture was cooled to 5° C., and the precipitated D,L-phenylalaninamide was collected by filtration. The collected crystals were washed with a small amount of water/acetone (weight ratio 1/1). The weight of the crystals after drying was 149.2 g, and the yield of D,L-phenylalaninamide based on the starting 1-benzylaminoacetonitrile was 90.9 mole %.

(A-2) 146.2 g of 1-benzylaminoacetonitrile and 0.5 g of a 20% by weight aqueous solution of sodium hydroxide were freshly added to the filtrate left after separation of D,L-phenylalaninamide in (A-1) above, and the same reaction and work-up as in (A-1) were carried out to form D,L-phenylalaninamide. The yield of D,L-phenylalaninamide based on the freshly added 1-benzylaminoacetonitrile was 100.2 mole %. When the same operation was repeated three times using the filtrate left after separation of D,L-phenylalaninamide, the yield of D,L-phenylalaninamide based on the freshly added 1-benzylaminoacetonitrile was 99.7 mole % on an average.

(B-1) Cultivation was carried out in the same way as in Example 32 except that *Lodderomyces elogisporus* (IFO 1676) was used as the seed microorganism, and D,L-phenylalaninamide was used as the alpha-amino acid amide added to the main culture medium. By centrifugation, 82 9 of living cells were obtained. The living cells had a water content of 79% by weight.

(B-2) 81.9 9 of D,L-phenylalaninamide obtained in (A) above and 903 9 of water were weighed and put into a 2-liter Erlenmeyer flask, and 39 g of the living cells obtained in (B-1) were added. The mixture was stirred at 50° C. for 5 hours.

After the reaction, the cells were removed by centrifugation, and water was removed under reduced pressure. Then, 200 ml of isobutanol was added and D-phenylalaninamide was dissolved under heat. The insoluble material was collected by filtration, and washed with a small amount of hot isobutanol to give L-phenylalanine as white crystals. The weight of the crystals after drying was 40.9 g, and the crystals had a specific rotation, $[\alpha]_D^{20}$, of $-34.5$ (H$_2$O, c=2). The yield of L-phenylalanime based on he starting 1-benzylaminoacetonitrile was 49.5 mole %.

The filtrate left after separation of the crystals weighed 230 g. Analysis by liquid chromatography showed that it contained 40.5 g of D-phenylalaninamide.

(C) A 500 ml three-necked flask equipped with a stirrer, a thermometer and a reflux condenser was charged with all the D-phenylalaninamide-containing i-butanol solution (filtrate) recovered in (B-2) and 0.25 g of sodium amide, and the mixture was stirred at 108° C. for 10 minutes.

After the reaction, i-butanol was removed from the reaction mixture by distillation under reduced pressure, and D,L-phenylalaninamide crystals were precipitated. The precipitated crystals were collected by filtration. The weight of the crystals after drying was 40.4 g. Analysis of the crystals by liquid chromatography showed that the ratio of remaining D,L-phenylalaninamide was 97%, and the ratio of racemization of D-phenylalaninamide was 94%.

(D) A 2-liter three-necked flask was charged with all the D,L-phenylalaninamide obtained in (C) above, all the microbial cells for each operation recovered in (B-2) above and 890 g of water. Furthermore, 41.0 g of D,L-phenylalaninamide obtained in (A) above and 13 g of the living cells obtained in (B-1) were freshly added, and the same reaction and work-up as in (B-2) were carried out.

The weight of the resulting L-phenylalanine crystals after drying was 38.8 g, and the crystals had a specific rotation, $[\alpha]_D^{20}$, of $-34.3$ (H$_2$O, c=2). The yield of L-phenylalanine based on the starting 1-benzylaminoacetonitrile corresponding to the freshly added D,L-phenylalaninamide was 93.9 mole %.

The filtrate left after separation of the crystals weighed 236 g, and analysis by liquid chromatography showed that it contained 41.2 g of D-phenylalaninamide.

When the operations of (C) and (D) were repeated twice using the D-phenylalaninamide-containing i-butanol solution recovered as above, the yield of L-phenylalanine based on the starting 1-benzylaminoacetonitrile corresponding to freshly added D,L-alaninamide was 94.3 to 93.7 mole %, and L-phenylalanine had a specific rotation, $[\alpha]_D^{20}$, of $-34.2$ to $-34.1$.

EXAMPLES 36-38

In each run, an L-alpha-amino acid was produced by repeating Example 33 except that each of the starting alpha-aminoacetonitrile indicated in Table 4 was used, and *Rhodosporidium toruloides* (IFO 0871) was used as a microorganism for biochemical hydrolysis of D,L-alpha-amino acid amide. The results are shown in Table 4.

TABLE 4

| Example | Starting alpha-amino acetonitrile | L-amino acid produced | Yield (mole % based on alpha-amino-acetonitrile) | $[\alpha]_D^{20}$ (degree) |
|---|---|---|---|---|
| 36 | 1-(beta-methyl-thioethyl)-amino-acetonitrile | L-methionine | 91.8–90.6 | +24.2–+23.9 |
| 37 | 1-isobutyl-amino-acetonitrile | L-leucine | 94.6–94.2 | +15.2–+14.8 |
| 38 | 1-(beta-carbox-amideethyl)-aminoaceto-nitrile | L-glutamine | 92.1–91.5 | +6.5–+6.3 |

Measuring conditions for $[\alpha]_D^{20}$:
6N—HCl, c = 8 for L-methionine
6N—HCl, c = 4 for L-leucine
H$_2$O, c = 4 for L-glutamine

EXAMPLE 39

Example 35 was repeated except that 1-indolylmethylaminoacetonitrile was used as the starting alpha aminoacetonitrile, *Pachysolen tannophilus* (IFO 1007) was used as the microorganism used for the biochemical hydrolysis of D,L-alpha-amino acid amide, and D,L-tryptophanamide was used as the alpha-amino acid amide to be added to the main culture medium.

The yield of L-tryptophan based on the starting material 1-indolylmethylaminoacetonitrile corresponding to D,L-tryptophanamide was 93.8 to 92.7 mole %, and the L-tryptophan had a specific rotation, $[\alpha]_D^{20}$, of $-31.3$ to $-30.9$ (H$_2$O, c=1).

As specifically shown above, the process of this invention makes it possible to produce important L-alpha-amino acids such as L-alanine, L-valine, L-leucine, L-isoleucine, L-serine, L-threonine, L-cysteine, L-cystine, L-methionine, L-lysine, L-arginine, L-asparagine, L-glutamine, L-phenylglycine, L-phenylalanine, L-tyrosine, L-tryptophan and L-histidine easily in high yields from D,L-alpha-amino acid amides which can be industrially obtained easily at low cost.

What is claimed is:

1. A process for racemization of an optically active alpha-amino amide, which comprises heating a D- or L-isomer of alpha-amino acid amide which is selected from the group consisting of alaninamide, valinamide, leucinamide, isoleucinamide, serinamide, threoninamide, cysteinamide, cystinamide, methioninamide, lysinamide, argininamide, aspartic amide, glutaminamide, phenylglycinamide, phenylalaninamide, tyrosinamide, tryptophanamide and histidinamide, at a temperature of 20° C. to 200° C. in the presence of a strongly basic compound and in the presence of an organic solvent or in the absence of any solvent to form a racemic mixture of the D- and L- alpha amino acid amides.

2. The process of claim 1 wherein the optically active alpha-amino acid amide is the D-alpha-amino acid amide.

3. The process of claim 1 wherein the optically active alpha-amino acid amide is the L-alpha-amino acid amide.

4. The process of claim 1 wherein the strongly basic compound is a strongly basic organic compound.

5. The process of claim 1 wherein the strongly basic compound is an organic quaternary ammonium compound.

6. The process of claim 1 wherein the strongly basic compound is a strongly basic inorganic compound.

7. The process of claim 1 wherein the strongly basic compound is an alkali metal compound or an alkaline earth metal compound.

8. The process of claim 1 wherein the strongly basic compound is used in an amount of 0.001 to 0.5 mole per mole of the optically active alpha-amino acid amide.

9. The process of claim 1 wherein the heating is carried out in the presence of a solvent.

10. The process of claim 9 wherein the solvent is used in an amount of not more than 100 parts by weight per part by weight of the optically active alpha-amino acid amide.

11. The process of claim 1 wherein the water content of the reaction system is controlled to not more than 1% by weight.

* * * * *